United States Patent

Muzilla et al.

[11] Patent Number: 5,938,611
[45] Date of Patent: Aug. 17, 1999

[54] METHOD AND APPARATUS FOR COLOR FLOW IMAGING USING CODED EXCITATION WITH SINGLE CODES

[75] Inventors: David John Muzilla, Mukwonago, Wis.; Richard Y. Chiao, Clifton Park, N.Y.; Anne Lindsay Hall, New Berlin, Wis.

[73] Assignee: General Electric Company, Milwaukee, Wis.

[21] Appl. No.: 09/048,760

[22] Filed: Mar. 26, 1998

[51] Int. Cl.[6] .................................................... A61B 8/06
[52] U.S. Cl. ............................................................ 600/455
[58] Field of Search .................................. 600/454–458; 73/861.25; 367/100, 135

[56] References Cited

U.S. PATENT DOCUMENTS

| 5,022,400 | 6/1991 | Walters | 600/455 |
| 5,224,482 | 7/1993 | Nikoonahad et al. | 600/454 |

OTHER PUBLICATIONS

Takeuchi, "Chirped Excitation for 100dB Time Sidelobe Echo Sounding," Proc. 1995 IEEE Ultrasonics Symp., pp. 1309–1314.

Takeuchi, "Coded Excitation for Harmonics Imaging", Proc. 1996 IEEE Ultrasonics Symp., pp. 1433–1436.

Welch, "Pulse Compression Ultrasound for Minimization of Transmitted Peak Power", Proc. 20th Annual Northeast Bioengineering Conference, Springfield, MA.

Welch et al., "Sidelobe Suppressed Spread Spectrum Pulse Compression for Ultrasonic Tissue Imaging," IEEE Trans. Ultrasonics, Ferroelec. & Freq. Control (accepted for publication 1997).

O'Donnell, "Coded Excitation System for Improving the Penetration of Real–Time Phased–Array Imaging Systems," IEEE Trans. Ultrason. Ferroelec. Freq. Cont., vol. 39, No. 3, May 1992, pp. 341–351.

*Primary Examiner*—Francis J. Jaworski
*Attorney, Agent, or Firm*—Dennis M. Flaherty; Christian G. Cabou; Phyllis Y. Price

[57] ABSTRACT

A color flow imaging technique uses coded excitation on transmit and pulse compression on receive. Coded excitation allows a long transmit pulse to be compressed on receive such that most energy is concentrated in a short interval. Multiple transmit firings of the same coded pulse sequence are focused at the same transmit focal position with the same transmit characteristics. The receive signals are compressed utilizing matched or mismatched filtering. These techniques can be used to maximize color flow sensitivity in deep-lying regions. Alternatively, for a given transmit acoustic burst length and dosage, the spatial resolution can be improved without compromising sensitivity.

25 Claims, 5 Drawing Sheets

METHOD AND APPARATUS FOR COLOR FLOW IMAGING USING CODED EXCITATION WITH SINGLE CODES

FIELD OF THE INVENTION

This invention generally relates to ultrasound color flow Doppler imaging of fluid flow fields. In particular, the invention relates to a method and an apparatus for imaging blood flowing in the human body by detecting Doppler shifting of ultrasonic echoes reflected from the flowing blood.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase, shift translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

In standard color flow processing, a high pass filter known as a wall filter is applied to the data before a color flow estimate is made. The purpose of this filter is to remove signal components produced by tissue surrounding the blood flow of interest. If these signal components are not removed, the resulting velocity estimate will be a combination of the velocities from the blood flow and the surrounding tissue. The backscatter component from tissue is many times larger than that from blood, so the velocity estimate will most likely be more representative of the tissue, rather than the blood flow. In order to get the flow velocity, the tissue signal must be filtered out.

In the color flow mode of a conventional ultrasound imaging system, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilohertz range. A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by a beamformer.

For example, the traditional color firing sequence is a series of firings (e.g., tone bursts) along the same position, which firings produce the respective receive signals:

$$F_1\ F_2\ F_3\ F_4\ldots F_M$$

where $F_i$ is the receive signal for the i-th firing and M is the number of firings in a packet. These receive signals are loaded into a corner turner memory, and a high pass filter (wall filter) is applied to each down range position across firings, i.e., in "slow time". In the simplest case of a $(1, -1)$ wall filter, each range point will be filtered to produce the respective difference signals:

$$(F_1 - F_2)\ (F_2 - F_3)\ (F_3 - F_4)\ldots (F_{M-1} - F_M)$$

and these differences are input to a color flow velocity estimator.

One of the primary advantages of Doppler ultrasound is that it can provide noninvasive and quantitative measurements of blood flow in vessels. Given the angle $\theta$ between the insonifying beam and the flow axis, the magnitude of the velocity vector can be determined by the standard Doppler equation:

$$v = c f_d / (2 f_0 \cos \theta) \tag{1}$$

where c is the speed of sound in blood, $f_0$ is the transmit frequency and $f_d$ is the motion-induced Doppler frequency shift in the backscattered ultrasound signal.

Because blood has a very low backscatter coefficient, in medical ultrasound color flow imaging, it is desirable to improve flow visualization by optimizing the SNR and resolution. Coded excitation is a well-known radar technique which is used in situations where the peak power of a transmitted signal cannot be increased but the average power can. This is often the case in medical ultrasound imaging, where system design limitations dictate the peak amplitude of the signal driving the transducer. Coded excitation can be used to increase signal-to-noise ratio by transmitting a longer pulse and/or to increase resolution by having a shorter decoded pulse.

In medical ultrasound imaging, longer signals, such as chirps, can be used to deliver higher average power values, and temporal resolution is restored by correlating the return signal with a matched filter. Chirps, however, are expensive to implement on a phased array ultrasound system due to the complexity of the electronics, so binary codes, or codes that can be easily represented digitally as a series of digits equal to +1, -1 or 0, are more practical. Binary codes are also preferred because they contain the most energy for a given peak amplitude and pulse duration. The problems with binary codes is that sidelobes generated in the correlation process generally degrade the image.

Acceptable sidelobe levels can be produced using a complementary set of transmit codes, e.g., Golay codes. A set of complementary-coded waveforms produce signals which, after autocorrelation and summation, yield a short pulse in range, due to the fact that the sidelobe levels produced by the autocorrelation of one code sequence are equal in magnitude but opposite in sign to the those of the complementary sequence. However, complementary transmit codes require paired firings which may degrade the system frame rate and/or the number of samples available for parameter estimation. Such systems also require circuitry for performing coherent summation. Lastly, the decoding may be degraded if flow velocities are too high or if adaptive techniques are used to rotate tissue signals in frequency for wall filtering before the coherent summation is performed.

There are situations where coded excitation on transmit and pulse compression on receive can be applied to color flow processing. One can gain SNR if, again, one is limited by the system peak power but not by the average power. In addition, color flow systems already tend to fire relatively long tone bursts to maximize the SNR, so one can gain additional spatial resolution over typical Doppler processing by using coded sequences.

SUMMARY OF THE INVENTION

The present invention is a method and an apparatus for improving the SNR and/or resolution in color flow ultrasound imaging by using coded excitation with a single code on transmit and pulse compression on receive. Coded excitation allows a long transmit pulse to be compressed on receive such that most energy is concentrated in a short interval. This technique can be used to maximize color flow sensitivity in deep-lying regions. Alternatively, for a given transmit acoustic burst length and dosage, the spatial resolution can be improved without compromising sensitivity.

The basic concept of the invention comprises modulating a specially designed code sequence based on a transmit burst (base sequence) of length P. The frequency of the transmit burst is typically in the megahertz range. A coded pulse sequence of n bursts is often referred to as an n-chip code. The coded pulse sequence, which has a length n×P, enables a larger acoustic dosage or a shorter base sequence to be used to interrogate the flowing blood. The output from the beamformer is compressed in time by passing it through a decoding finite impulse response (FIR) filter. Some coded waveforms are best compressed by matched filtering, i.e., using a set of FIR filter coefficients that is an identical copy of the n-chip code. However, sometimes more desirable compression effects are achieved by mismatched filtering using FIR filters that have more than n filter coefficients or have coefficients which differ from the original n-chip code. The output of the decoding (i.e., compression) filter is a compressed signal pulse of length equal or close to the original transmit burst length P, but whose amplitude is that produced by the n-times-longer coded pulse sequence. This technique has no adverse effects on frame rate, does not require coherent summation, has no degradation in the number of samples available for parameter estimation, and has much less chance of improper decoding due to high velocities or adaptive rotation.

In accordance with the broad concept of the invention, the beamformer output can be either an RF signal or its I/Q components. Preferably, the beamformer output is decoded and then demodulated. In the case of an RF beamformer output, the demodulator transforms the compressed RF signal into its I/Q components for color flow processing. If demodulation precedes decoding, then the decoding filter must be designed to compress the demodulated signal.

DETAILED DESCRIPTION OF THE PREFERRED EMBODIMENTS

Figure 1:
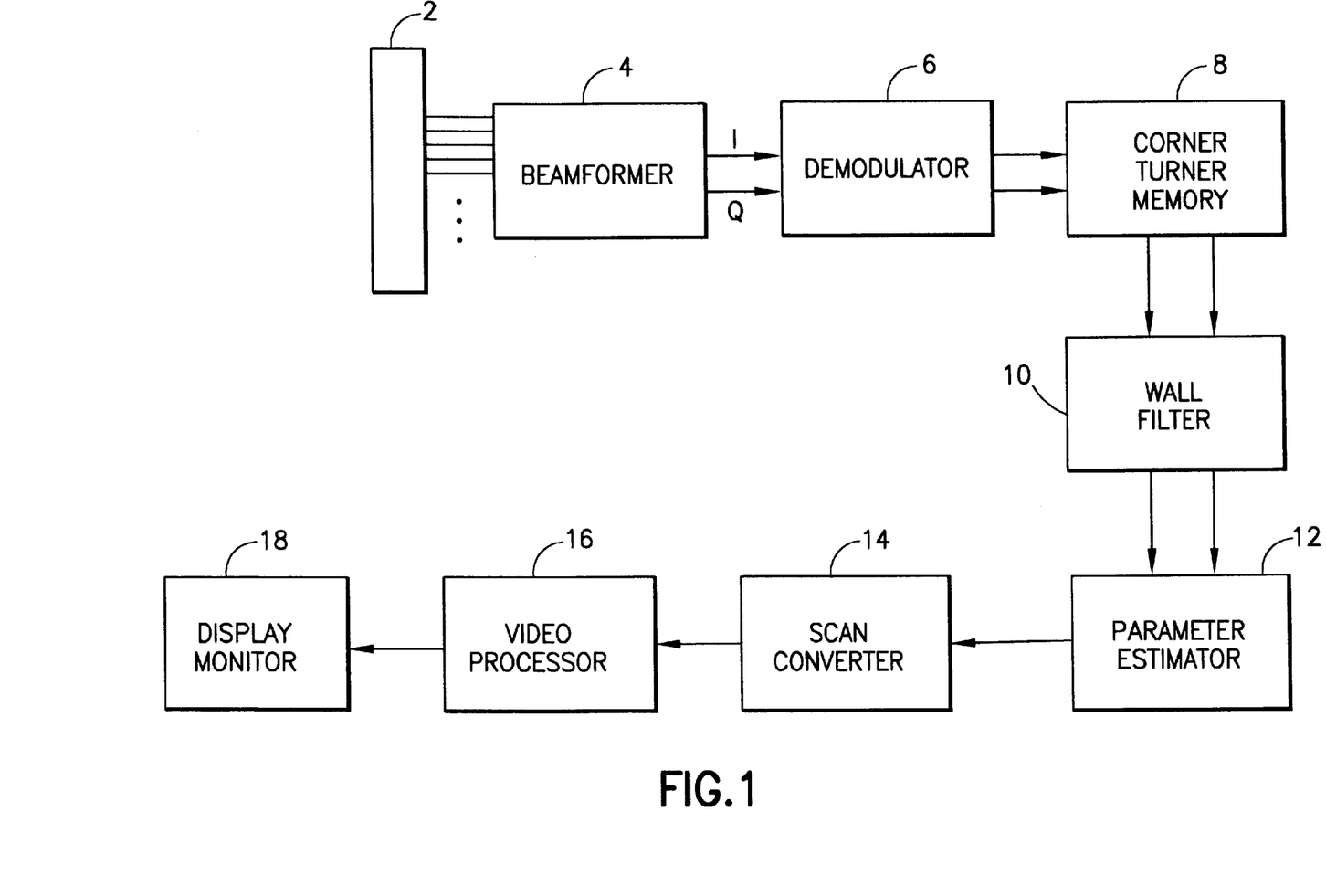
FIG. 1 is a block diagram showing the signal processing chain for a conventional color flow ultrasound imaging system.

Referring to FIG. 1, the basic signal processing chain for a color flow imaging system comprises an ultrasound transducer array 2, which is activated to transmit coded pulse sequences comprising phase-coded tone bursts of length P which are fired repeatedly at the PRF. The return RF signals are detected by the transducer elements and received by the respective receive channels in the beamformer 4. The beamformer sums the delayed channels data and outputs either RF or in-phase and quadrature (I/Q) data. The latter alternative is illustrated in FIG. 1.

In the conventional system, the frequencies of the beamformer outputs are shifted to baseband by a demodulator 6. The demodulated I/Q components are stored in a corner turner memory 8, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through respective wall filters 10, which reject any clutter corresponding to stationary or very slow-moving tissue. The filtered outputs are then fed into a parameter estimator 12, which converts the range cell information into the intermediate autocorrelation parameters N, D, and R(0). N and D are the numerator and denominator for the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} + Q_i Q_{i+1}) \quad (3)$$

where $I_i$ and $Q_i$ are the demodulated, basebanded input data for firing i, and M is the number of firings in the packet. R(0) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2} \quad (4)$$

A processor converts N and D into a magnitude and phase for each range cell. The equations used are as follows:

$$|R(T)| = \sqrt{N^2 + D^2} \quad (5)$$

$$\phi(R(T)) = \tan^{-1}\left[\frac{N}{D}\right] \quad (6)$$

The parameter estimator processes the magnitude and phase values into estimates of power, velocity and turbulence. The phase is used to calculate the mean Doppler frequency, which is proportional to the velocity as shown below; R(0) and |R(T)| (magnitude) are used to estimate the turbulence.

The mean Doppler frequency in hertz is obtained from the phase of N and D and the pulse repetition time T:

$$\bar{f} = \frac{1}{2\pi T}\tan^{-1}\left[\frac{N}{D}\right] = \frac{1}{2\pi T}(\phi(R(T))) \qquad (7)$$

The mean velocity is calculated using the Doppler shift equation below. Since θ, the angle between the flow direction and the sampling direction, is not known, cos θ is assumed to be 1.0.

$$\bar{v} = \frac{\bar{f}}{f_0}\frac{c}{2\cos\theta} \qquad (8)$$

Note that the parameter estimator does not calculate the mean Doppler frequency as an intermediate output, but calculates v̄ directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions, R(0) and R(T) respectively. The exact autocorrelation functions are approximated by finite sums over the known data in the number of firings in a packet:

$$\sigma^2 = \frac{2}{(2\pi T)^2}\left[1 - \frac{|R(T)|}{R(0)}\right] \qquad (9)$$

The mean value signal φ (R(T)) is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(0) indicates the amount of the returned power in the Doppler-shifted flow signal.

The color estimates are sent to a scan converter 14, which converts the color images into X–Y format for video display. The scan-converted frames are passed to a video processor 16, which basically maps the video data to a display color map for video display. The color flow image frames are then sent to the video monitor 18 for display. Typically, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

Figure 2:
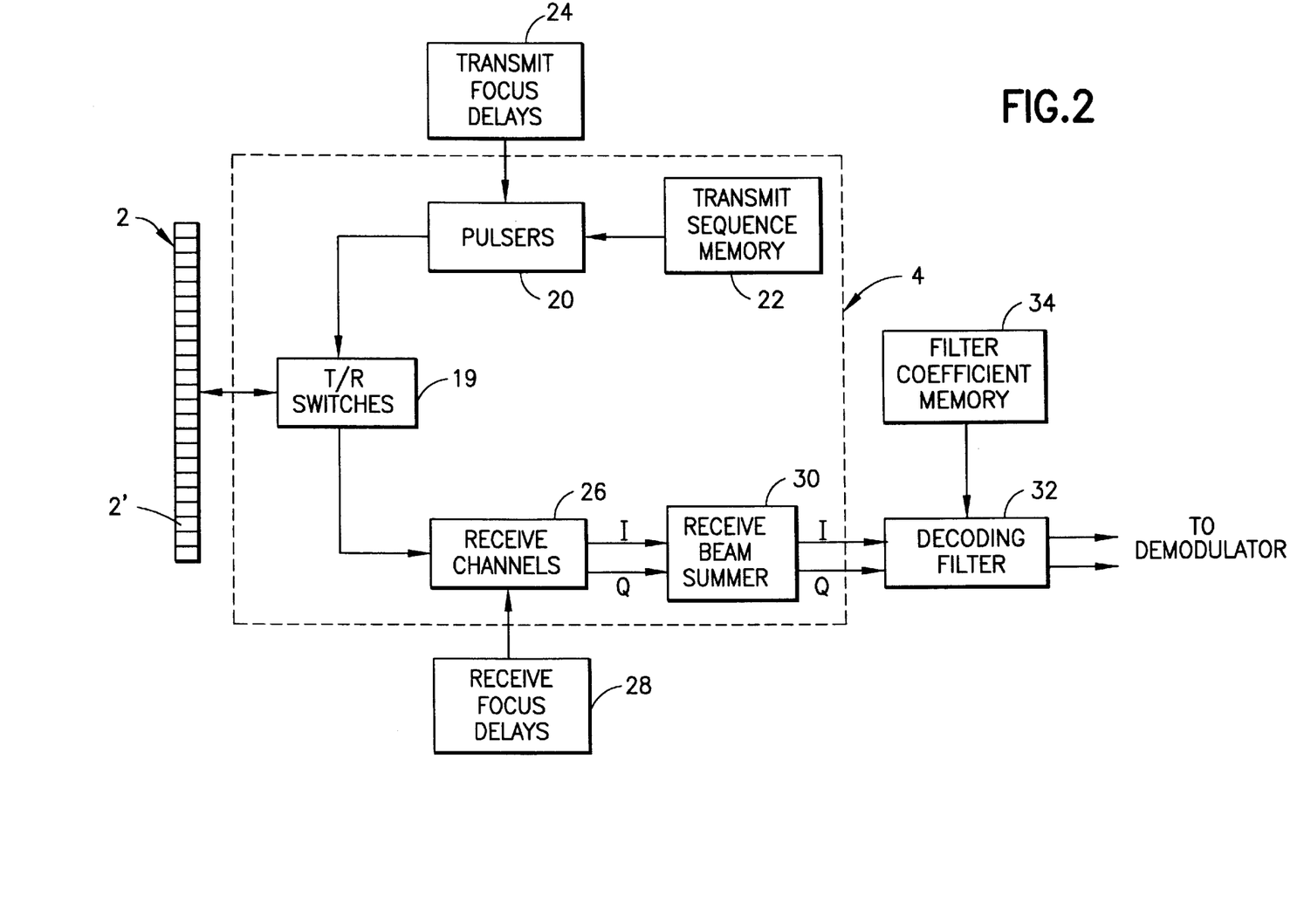
FIG. 2 is a block diagram showing the front end of a color flow ultrasound imaging system in accordance with a first preferred embodiment of the invention.

The preferred embodiment of the invention is shown in FIG. 2. For each transmit firing, each transducer element 2' in the transmit aperture is pulsed with a coded pulse sequence output by a respective bipolar pulser 20. The coded pulse sequence is derived from a coded transmit sequence formed by convolving a transmit code (e.g., a Barker code) with a base sequence (e.g., a tone burst). For an n-digit transmit code, the coded pulse sequence comprises n chips. In accordance with the preferred embodiments of the invention, the bipolar pulsers generate a polarity-coded pulse sequence in which the phase of pulses encoded with a +1 is 0°, while the phase of pulses encoded with a −1 is 180°. The coded transmit sequence for controlling the phase of pulses output by each bipolar pulser 20 is stored in a transmit sequence memory 22.

The bipolar pulsers 20 drive the elements 2' of transducer array 2 such that the ultrasonic energy produced is focused in a beam for each transmit firing. To accomplish this, transmit focus time delays 24 are imparted to the respective pulsed waveforms output by the pulsers in response to the coded transmit sequence. By appropriately adjusting the transmit focus time delays in a conventional manner, the ultrasonic beam can be focused at a desired transmit focal position. The coded pulse sequences are sent from the pulsers to the transducer elements via respective transmit/receive (T/R) switches 19. The T/R switches 19 are typically diodes which protect the receive electronics from the high voltages generated by the transmit electronics. The transmit signal causes the diodes to shut off or limit the signal to the receiver.

After each transmit, the transducer elements 2' are switched to receive mode to accept the returning echoes backscattered from the object being scanned. These return signals are fed to respective receive channels 26 of the receive beamformer, also via the T/R switches 19. The receive beamformer tracks echoes under the direction of a master controller (not shown). The receive beamformer imparts the proper receive focus time delays 28 to the received echo signal and sums them to provide an echo signal which accurately indicates the total ultrasonic energy reflected from a succession of ranges corresponding to a particular transmit focal position. In accordance with the embodiment depicted in FIG. 2, the beamformer also transforms the RF signal into its I/Q components by means of Hilbert bandpass filtering in each receive channel. The I/Q components are then summed in receive summer 30 for each transmit firing. Hilbert bandpass filtering can alternatively be performed after beam summation.

The I/Q components for each transmit firing are then decoded by a respective decoding filter 32 which outputs a compressed pulse in accordance with the present invention. For an n-digit transmit code, the decoding filter 32 is preferably an FIR filter having M filter taps (M≧n) for receiving a set of M filter coefficients from a filter coefficient memory 34. In accordance with a preferred embodiment, the filter coefficients $c_0, c_1, \ldots, c_{M-1}$ have scalar values which, when convolved with the n-digit transmit code, produce a compressed receive pulse sequence. [The filter coefficients, like the transmit and receive time delays and the coded transmit sequences, can be supplied by the master controller.]

Figure 3:
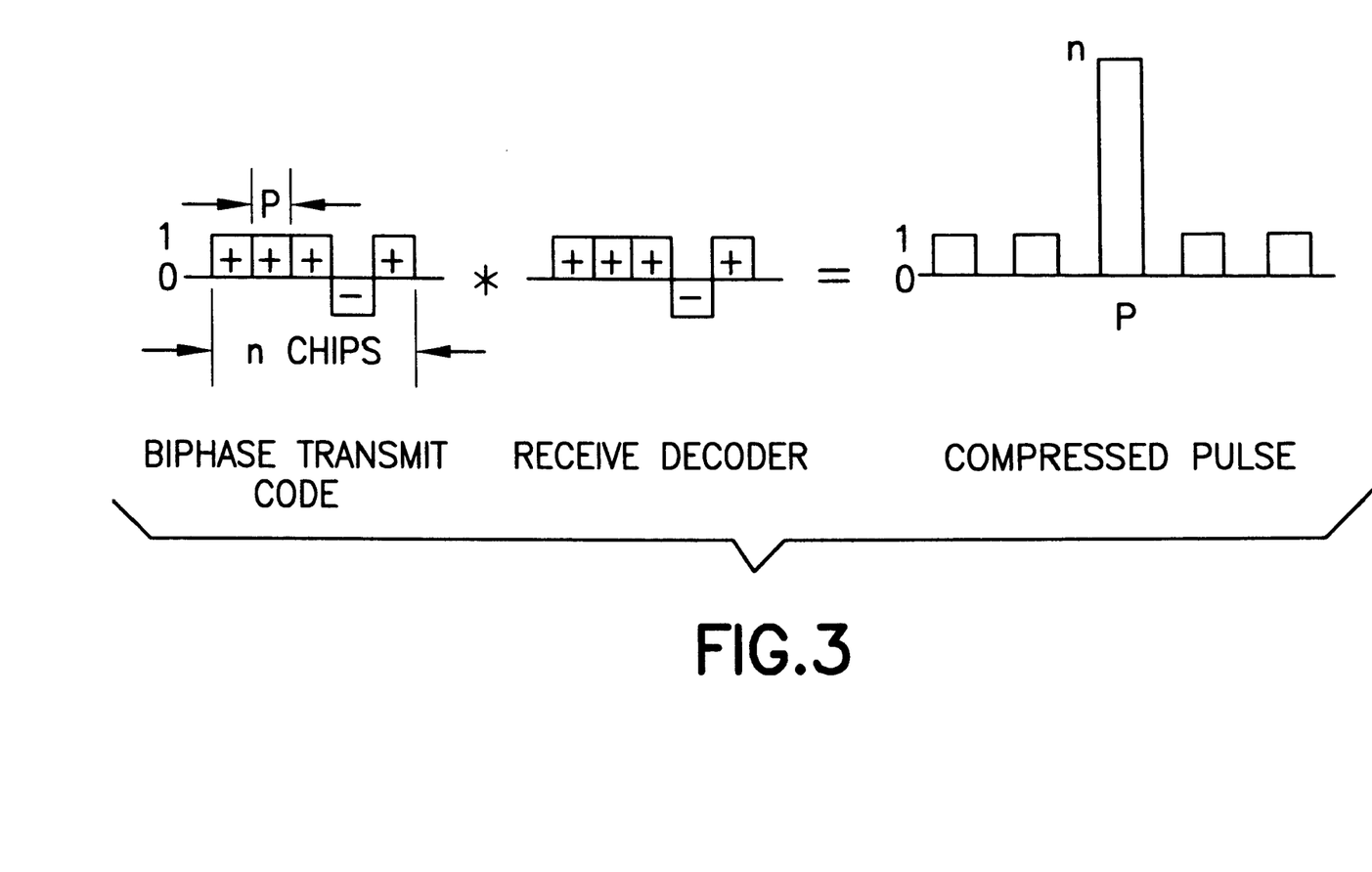
FIG. 3 is a schematic illustrating a compressed pulse resulting from convolution of a 5-bit biphase transmit code with matched filter coefficients of a decoding filter in accordance with a first variation of the first preferred embodiment of the invention.

As an example, FIG. 3 shows a 5-chip code sequence from the Barker code family. Barker codes are biphase (or binary) code sequences of various lengths up to n=13. [The set of all Barker codes is disclosed in an article by Welch et al. entitled "Sidelobe suppressed spread spectrum pulse compression for ultrasonic tissue imaging," IEEE Trans Ultrasonics, Ferroelec., and Freq. Control (accepted for publication, Aug. 1997), the contents of which are incorporated by reference herein.] If the 5-bit Barker code [1,1,1,−1,1] is decoded by a matching FIR filter (i.e., a filter having filter coefficients identical to the digits of the transmit code) as shown in FIG. 3, the compression ratio achieved is n=5, which corresponds to a SNR gain of 7 dB. However, as seen in FIG. 3, the main pulse in the decoder filter output is surrounded by pulses of smaller amplitude. These small-amplitude pulses correspond to axial or range sidelobes that are 1/n times lower in amplitude compared to the main lobe.

Figure 4:
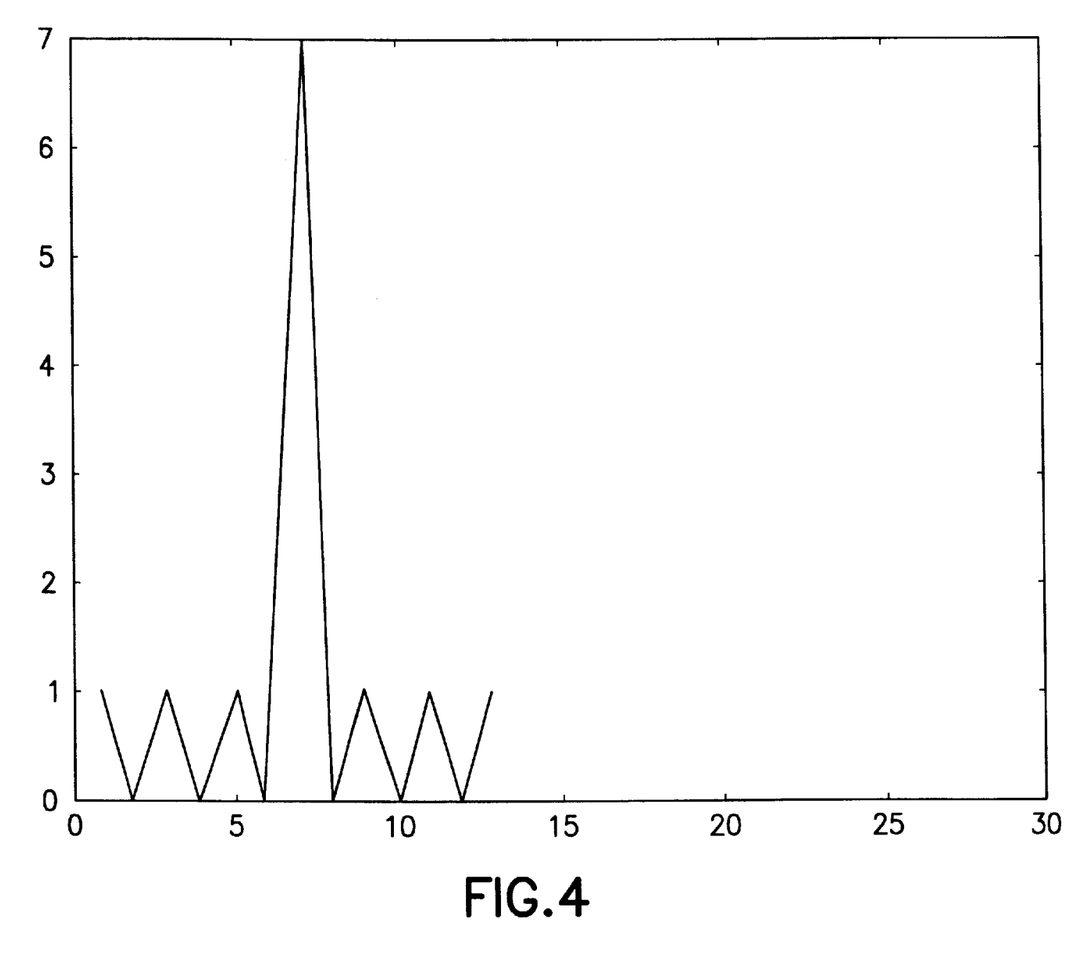
FIG. 4 is a graph showing a compressed pulse resulting from convolution of a 7-bit biphase transmit code with the filter coefficients of a matching filter in accordance with a second variation of the first preferred embodiment of the invention.

Another code which is suitable for use in the invention is the 7-bit Barker code [1,1,1,−1,−1,1,−1], which transmit code is convolved with a base pulse sequence to produce the transmit code sequence. The base pulse sequence in this example is a two-cycle bipolar waveform having a center frequency of 5 MHz, which is sampled at 40 MHz, i.e., [1,1,1,1,−1,−1,−1, −1,1,1,1,1,−1,−1,−1,−1]. The full 7-chip transmit code sequence is as follows:

$$[1, 1, 1, 1, -1, -1, -1, -1, 1, 1, 1, 1, -1, -1, -1, -1]$$

$$[1, 1, 1, 1, -1, -1, -1, -1, 1, 1, 1, 1, -1, -1, -1, -1]$$

$$[1, 1, 1, 1, -1, -1, -1, -1, 1, 1, 1, 1, -1, -1, -1, -1]$$

$$[-1, -1, -1, -1, 1, 1, 1, 1, -1, -1, -1, -1, 1, 1, 1, 1]$$

$$[-1, -1, -1, -1, 1, 1, 1, 1, -1, -1, -1, -1, 1, 1, 1, 1]$$

$$[1, 1, 1, 1, -1, -1, -1, -1, 1, 1, 1, 1, -1, -1, -1, -1]$$

$$[-1, -1, -1, -1, 1, 1, 1, 1, -1, -1, -1, -1, 1, 1, 1, 1]$$

The decoding or autocorrelation is achieved on receive by the decoding filter. The appropriate decoding filter is designed based on the transmit code, the demodulation frequency (if decoding follows demodulation) and the amount of downsampling performed on receive. FIG. 4 shows the pulse compression effected using a decoding filter with filter coefficients that match the transmit code [1,1,1,−1,−1,1,−1]. The peak spike is at 7 and the sidelobes are at 1 (−17 dB down from the peak). Theoretically, the above waveform would transmit the energy of a 14-cycle 5-MHz waveform, but achieve the range resolution on receive of a 2-cycle 5-MHz base pulse waveform (i.e., a 7-to-1 improvement in resolution).

Figure 5:
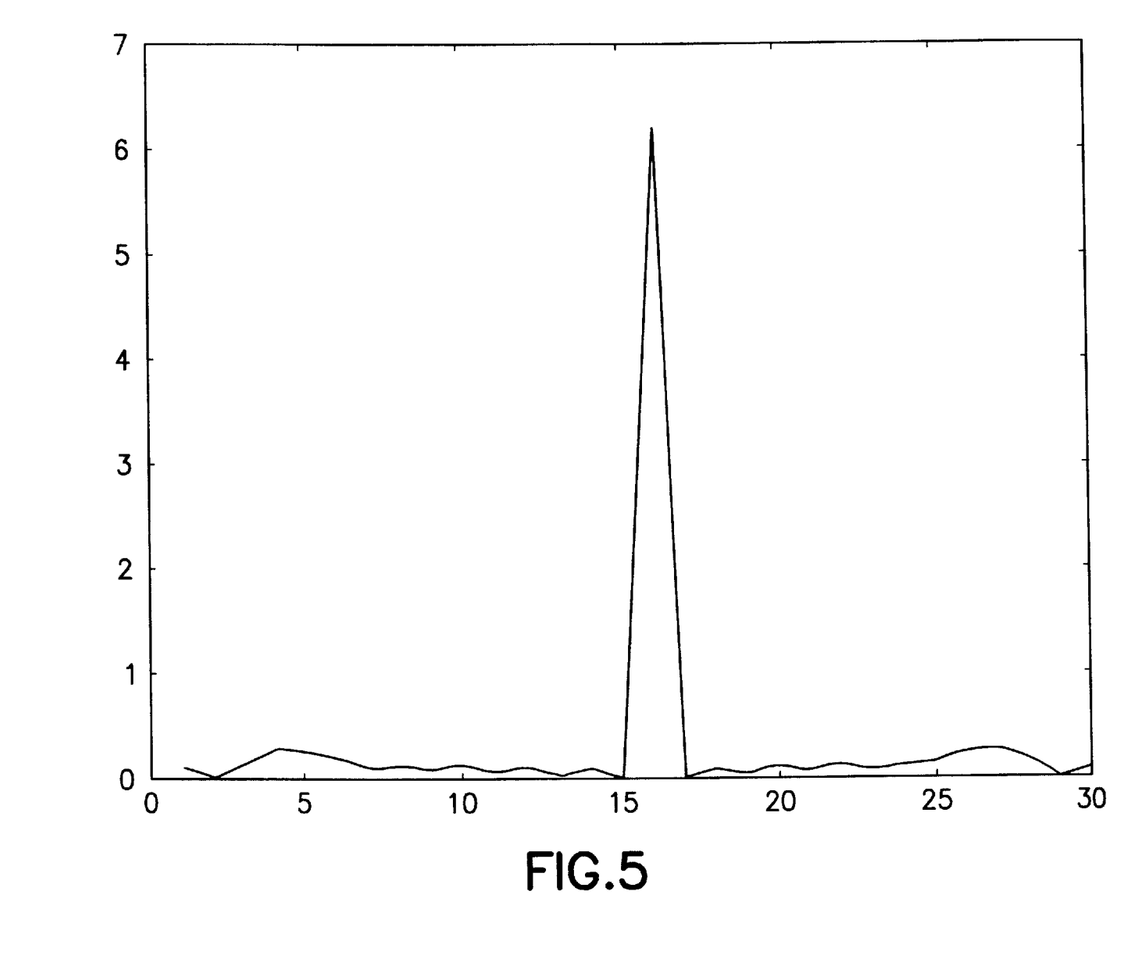
FIG. 5 is a graph showing a compressed pulse resulting from convolution of the same 7-bit biphase transmit code with the filter coefficients of a mismatch filter in accordance with a third variation of the first preferred embodiment of the invention.

Among all biphase codes, Barker codes are well known for their property of having the smallest sidelobes possible when decoded by a matched filter. However, it should be noted that for any single transmit code, the sidelobes can often be suppressed via mismatched filtering at the expense of decreased signal gain and/or main lobe broadening (decreased range resolution). An example of a mismatched filter for the 7-bit Barker code [1,1,1,−1,−1,1,−1] is a 24-tap filter whose coefficients are as follows: [0.1001, −0.1084, 0.1488, −0.2186, 0.2994, −0.3219, 0.2524, −0.2186, 0.3898, −0.8812, 1.2050, −0.8265, −0.3764, 0.8265, 1.1992, 0.8812, 0.3800, 0.2186, 0.2294, 0.3219, 0.2765, 0.2186, 0.1266, 0.1084]. FIG. 5 shows convolution of the 7-bit Barker code with this 24-tap mismatched filter. The coefficients of this mismatched filter were determined using a well-known least squares technique [see, e.g., Robinson et al., Geophysical Signal Analysis, Englewood Cliffs, Prentice-Hall (1980)] to minimize the sidelobes while trying to preserve the peak spike. With this mismatch filtering technique, the sidelobes have been reduced another 10 dB (−27 dB below the peak), but with a loss in the peak level of about 1 dB. By using fewer or more taps for the mismatched filter, the sidelobes can be increased or decreased, resulting in a decrease or increase in peak signal loss. In general, greater sidelobe suppression can be achieved using longer mismatched FIR filters.

The decoding filters output the respective pulse compressed signals to the demodulator 6 (see FIG. 1). These pulse-compressed I/Q signals are shifted in frequency by demodulator 6. One way of achieving this is to multiply the input signal by a complex sinusoidal $e^{i2\pi f_d t}$, where $f_d$ is the frequency shift required to bring the signal spectrum to baseband.

The decoding FIR filters 32 can be implemented in software or hardware at the beamformer output, as shown in FIG. 2, or at the demodulator output (not shown). In the latter case, the decoding filter coefficients must be matched or mismatched to the demodulated signals. For the case when the demodulator shifts by discrete frequencies $f_d = k/2t_b$, where k is any positive integer and $t_b$ is the duration of the transmit base sequence, the sinusoidal becomes real and the same set of filter coefficients are input to both decoding filters for the I and Q components, which thus form a real filter. In the cases when $f_d \neq k/2t_b$, the I and Q decoding filters receive different sets of filter coefficients and thus form a complex filter. In the latter case, the filter coefficients are either matched or mismatched to the respective demodulated signal component.

The foregoing preferred embodiments have been disclosed for the purpose of illustration. Variations and modifications of the concept of the invention will be readily apparent to persons skilled in the art. In particular, the transmit pulse sequences may be amplitude-coded, rather than phase- or polarity-coded. In addition, polyphase codes can be used in place of biphase codes. All such variations and modifications are intended to be encompassed by the claims set forth hereinafter.

We claim:

1. A system for imaging flow of ultrasound scatterers, comprising:

an ultrasound transducer array for transmitting ultrasound waves and detecting ultrasound echoes reflected by said ultrasound scatterers, said transducer array comprising a multiplicity of transducer elements;

transmit means coupled to said transducer array for pulsing selected transducer elements which form a transmit aperture with a coded pulse sequence during first and second transmit firings focused at a transmit focal position and have substantially the same transmit characteristics, said coded pulse sequence being a function of a transmit code convolved with a base pulse sequence;

receive means coupled to said transducer array for receiving first and second sets of signals from selected transducer elements which form a receive aperture subsequent to said first and second transmit firings respectively;

means for forming first and second beamsummed signals respectively derived from said first and second sets of signals;

a decoding filter for compressing said first and second beamsummed signals to form first and second compressed pulse sequences respectively;

a high-pass filter for high-pass filtering said first and second compressed pulse sequences to form a first high-pass-filtered signal;

means for estimating a flow parameter as a function of at least said first high-pass-filtered signals to form a flow image signal; and means for displaying an image which is a function of said flow image signal.

2. The system as defined in claim 1, wherein said flow parameter is power.

3. The system as defined in claim 1, wherein:

said transmit means pulse said selected transducer elements which form said transmit aperture with said coded pulse sequence during a third transmit firing focused at said transmit focal position;

said receive means receive a third set of signals from said selected transducer elements which form said receive aperture subsequent to said third transmit firing;

said forming means form a third beamsummed signal derived from said third set of signals;

said decoding filter compresses said third beamsummed signal to form a third compressed pulse sequence;

said high-pass filter high-pass filters said second and third compressed pulse sequences to form a second high-pass-filtered signal; and said flow parameter estimating means estimate said flow parameter as a function of at least said first and second high-pass-filtered signals to form said flow image signal.

4. The system as defined in claim 3, wherein said flow parameter is velocity.

5. The system as defined in claim 3, wherein said flow parameter is variance.

6. The system as defined in claim 1, wherein said decoding filter is programmed with a set of filter coefficients which match said transmit code.

7. The system as defined in claim 1, wherein said decoding filter is programmed with a set of filter coefficients which are mismatched to said transmit code.

8. The system as defined in claim 1, wherein said high-pass filter comprises means for subtracting one of said first and second compressed pulse sequences from the other of said first and second compressed pulse sequences.

9. The system as defined in claim 1, wherein said transmit code is a Barker code.

10. The system as defined in claim 1, wherein said transmit code is a binary code.

11. A method for imaging ultrasound scatterers, comprising the steps of:

producing a coded pulse sequence which is a function of a transmit code convolved with a base pulse sequence;

driving a first set of transducer elements forming a transmit aperture in a transducer array with said coded pulse sequence during a first transmit firing focused at a transmit focal position;

receiving a first set of echo signals from a second set of transducer elements forming a receive aperture in the transducer array subsequent to said first transmit firing;

forming a first beamsummed signal derived from said first set of echo signals;

compressing said first beamsummed signal to form a first compressed pulse sequence;

driving said first set of transducer elements forming said transmit aperture with said coded pulse sequence during a second transmit firing focused at said transmit focal position;

receiving a second set of echo signals from said second set of transducer elements forming said receive aperture subsequent to said second transmit firing;

forming a second beamsummed signal derived from said second set of echo signals;

compressing said second beamsummed signal to form a second compressed pulse sequence;

high-pass filtering said first and second compressed pulse sequences to form a first high-pass-filtered signal;

estimating a flow parameter as a function of at least said first high-pass-filtered signal to form a flow image signal; and displaying an image which is a function of said flow image signal.

12. The method as defined in claim 11, wherein said flow parameter is power.

13. The method as defined in claim 11, further comprising the steps of:

driving said first set of transducer elements forming said transmit aperture with said coded pulse sequence during a third transmit firing focused at said transmit focal position;

receiving a third set of echo signals from said second set of transducer elements forming said receive aperture subsequent to said third transmit firing;

forming a third beamsummed signal derived from said third set of echo signals;

compressing said third beamsummed signal to form a third compressed pulse sequence;

high-pass filtering said second and third compressed pulse sequences to form a second high-pass-filtered signal; and estimating said flow parameter as a function of at least said first and second high-pass-filtered signals to form said flow image signal.

14. The method as defined in claim 13, wherein said flow parameter is velocity.

15. The method as defined in claim 13, wherein said flow parameter is variance.

16. The method as defined in claim 11, wherein said transmit code is a Barker code.

17. The method as defined in claim 11, wherein said transmit code is a binary code.

18. The method as defined in claim 11, wherein said compressing steps are carried out by filtering said first and second beamsummed signals using a set of filter coefficients which match said transmit code.

19. The method as defined in claim 11, wherein said compressing steps are carried out by filtering said first and second beamsummed signals using a set of filter coefficients which are mismatched to said transmit code.

20. A system for imaging flow of ultrasound scatterers, comprising:

an ultrasound transducer array for transmitting ultrasound waves and detecting ultrasound echoes reflected by said ultrasound scatterers, said transducer array comprising a multiplicity of transducer elements;

transmit means coupled to said transducer array for pulsing selected transducer elements which form a transmit aperture with a coded pulse sequence during first and second transmit firings which are focused at substantially the same transmit focal position, said coded pulse sequence being a function of a transmit code convolved with a base pulse sequence;

receive means coupled to said transducer array for receiving first and second sets of signals from selected transducer elements which form a receive aperture subsequent to said first and second transmit firings respectively;

means for forming a first beamsummed signal derived from said first set of signals, and a second beamsummed signal derived from said second set of signals;

means for demodulating said first beamsummed signal to form a first demodulated signal, and demodulating said second beamsummed signal to form a second demodulated signal;

a decoding filter for compressing said first and second demodulated signals to form first and second compressed pulse sequences respectively;

a high-pass filter for high-pass filtering said first and second compressed pulse sequences to form a first high-pass-filtered signal;

means for estimating a flow parameter as a function of at least said first high-pass-filtered signal to form a flow image signal; and means for displaying an image which is a function of said flow image signal.

21. The system as defined in claim 20, wherein said flow parameter is power.

22. The system as defined in claim 20, wherein:

said transmit means pulse said selected transducer elements which form said transmit aperture with said coded pulse sequence during a third transmit firing focused at said transmit focal position;

said receive means receive a third set of signals from said selected transducer elements which form said receive aperture subsequent to said third transmit firing;

said forming means form a third beamsummed signal derived from said third set of signals;

said demodulating means demodulate said third beamsummed signal to form a third demodulated signal;

said decoding filter compresses said third demodulated signal to form a third compressed pulse sequence;

said high-pass filter high-pass filters said second and third compressed pulse sequences to form a second high-pass-filtered signal; and said flow parameter estimating means estimate said flow parameter as a function of at least said first and second high-pass-filtered signals to form said flow image signal.

23. The system as defined in claim 22, wherein said flow parameter is velocity.

24. The system as defined in claim 22, wherein said flow parameter is variance.

25. The system as defined in claim 20, wherein said high-pass filter comprises means for subtracting one of said first and second compressed pulse sequences from the other of said first and second compressed pulse sequences.

* * * * *